United States Patent
Abdel-Rahman

(10) Patent No.: US 11,970,433 B1
(45) Date of Patent: *Apr. 30, 2024

(54) SYNTHETIC ROUTE TO 2,2'-DIMETHYL-4,4'-DIIODOAZOBENZENE VIA HOMO-OXIDATIVE CROSS-COUPLING OF ARYL DIAZONIUM SALT USING CU-CATALYZED SANDMEYER-STYLE REACTION

(71) Applicant: KING FAISAL UNIVERSITY, Al Hasa (SA)

(72) Inventor: Obadah Subhi Abdel-Rahman, Al-Ahsa (SA)

(73) Assignee: KING FAISAL UNIVERSITY, Al Hasa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/534,171

(22) Filed: Dec. 8, 2023

(51) Int. Cl.
   *C07C 245/12* (2006.01)
   *B01J 27/055* (2006.01)
   *C07B 63/00* (2006.01)

(52) U.S. Cl.
   CPC .......... *C07C 245/12* (2013.01); *B01J 27/055* (2013.01); *C07B 63/00* (2013.01)

(58) Field of Classification Search
   CPC .............................. C07C 245/12; C07B 63/00
   See application file for complete search history.

(56) References Cited

U.S. PATENT DOCUMENTS

| 9,827,088 B2 | 11/2017 | Risser et al. |
| 2014/0211293 A1 | 7/2014 | Leguijt et al. |

FOREIGN PATENT DOCUMENTS

| CN | 105367442 A | 3/2016 |
| KR | 101713303 B1 | 3/2017 |

OTHER PUBLICATIONS

Koehl et al., Synthesis, 2014, 46(17), 2376-2382. (Year: 2014).*
Abboud, et al. "Novel family of periodic mesoporous organosilicas containing azobenzene within the pore walls", Microporous and Mesoporous Materials, 249 (2017): 157-164.
Akhtar, et al. "Recent trends in the chemistry of Sandmeyer reaction: a review", Mol Divers. Jun. 2022;26(3):1837-1873.
Koehl, et al. "Synthesis of functionalized azobiphenyls and azoterphenyls with improved solubilities for switching applications", Synthesis (2014), 46(17), 2376-2382, Abstract only.
Schultzke, et al. "Active Ester Functionalized Azobenzenes as Versatile Building Blocks", Molecules. Jun. 26, 2021;26(13):3916.

* cited by examiner

*Primary Examiner* — Laura L Stockton
(74) *Attorney, Agent, or Firm* — Nath, Goldberg & Meyer; Richard C. Litman

(57) ABSTRACT

A new synthetic route to a 2,2'-dimethyl-4,4'-diiodoazobenzene compound using homo-oxidative cross-coupling of an aryl diazonium salt using a Cu-catalyzed Sandmeyer-style reaction.

11 Claims, No Drawings

SYNTHETIC ROUTE TO 2,2'-DIMETHYL-4,4'-DIIODOAZOBENZENE VIA HOMO-OXIDATIVE CROSS-COUPLING OF ARYL DIAZONIUM SALT USING CU-CATALYZED SANDMEYER-STYLE REACTION

BACKGROUND

1. Field

The disclosure of the present patent application relates to a new synthetic route to obtain a 2,2'-dimethyl-4,4'-diiodoazobenzene compound using homo-oxidative cross-coupling of aryl diazonium salt using a Cu-catalyzed Sandmeyer-style reaction.

2. Description of the Related Art

Cross coupling systems play an effective role in the development of various chemical industrial processes. Azo-arylenes and its similar related derivatives have been intensively investigated and attracted enormous interests due to straightforward derivative synthesis step through classical homo-oxidative cross-coupling of aryl diazonium salts using Cu-catalyzed Sandmeyer-style reactions. Moreover, these chromophores usually show a strong $\pi \rightarrow \pi^*$ transition in the UV-Vis regime which can be predictively tuned by introducing substituents on the aryl rings.

Accordingly, there remains a need for novel methods for making certain azoarylene compounds and their related derivatives.

SUMMARY

The present subject matter relates to a new procedure for synthesis of 2,2'-dimethyl-4,4'-diiodoazobenzene using homo-oxidative cross-coupling of an aryl diazonium salt using a Cu-catalyzed Sandmeyer-style reaction.

In one embodiment, the present subject matter may relate to a method of making a 2,2'-dimethyl-4,4'-diiodoazobenzene compound, the method comprising:

suspending 4-iodo-2-methylaniline in a mixture of HCl and water to obtain a suspension;

diazotizing the amine group of the 4-iodo-2-methylaniline by slowly adding a solution of $NaNO_2$ in water to the suspension to obtain a mixture;

stirring the mixture to obtain a stirred mixture;

transferring the stirred mixture into a solution of $CuSO_4 \cdot 5H_2O$, $NH_4OH$, $NH_2OH$, and NaOH in water to obtain a reaction mixture;

heating the reaction mixture to obtain a heated reaction mixture;

cooling and acidifying the heated reaction mixture to obtain an acidified mixture;

obtaining a crude residue;

extracting organic layers of the crude reside; and purifying the organic layers to obtain the 2,2'-dimethyl-4,4'-diiodoazobenzene compound having the formula:

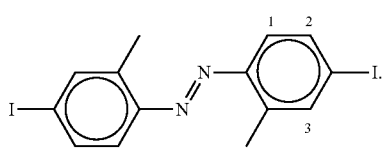

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a new procedure for synthesis of 2,2'-dimethyl-4,4'-diiodoazobenzene using homo-oxidative cross-coupling of an aryl diazonium salt using a Cu-catalyzed Sandmeyer-style reaction.

In one embodiment, the present subject matter may relate to a method of making a 2,2'-dimethyl-4,4'-diiodoazobenzene compound, the method comprising:
  suspending 4-iodo-2-methylaniline in a mixture of HCl and water to obtain a suspension;
  diazotizing the amine group of the 4-iodo-2-methylaniline by slowly adding a solution of NaNO$_2$ in water to the suspension to obtain a mixture;
  stirring the mixture to obtain a stirred mixture;
  transferring the stirred mixture into a solution of CuSO$_4$·5H$_2$O, NH$_4$OH, NH$_2$OH, and NaOH in water to obtain a reaction mixture;
  heating the reaction mixture to obtain a heated reaction mixture;
  cooling and acidifying the heated reaction mixture to obtain an acidified mixture;
  obtaining a crude residue;
  extracting organic layers of the crude reside; and
  purifying the organic layers to obtain the 2,2'-dimethyl-4,4'-diiodoazobenzene compound having the formula:

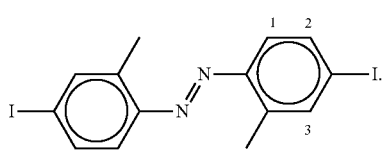

The present subject matter relates to a new procedure for synthesis of 2,2'-dimethyl-4,4'-diiodoazobenzene using homo-oxidative cross-coupling of an aryl diazonium salt using a Cu-catalyzed Sandmeyer-style reaction.

In another embodiment, the present subject matter relates to a method of making the 2,2'-dimethyl-4,4'-diiodoazobenzene compound according to Scheme 1:

Scheme 1

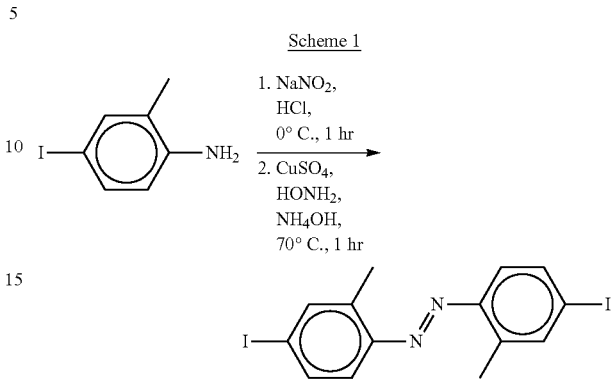

In one embodiment in this regard, the diazotizing step can be conducted at a temperature of about 0° C.

In another embodiment in this regard, the mixture can be stirred at about 0° C. for about 1 hour.

In a further embodiment, the reaction mixture can be stirred at about 25° C. prior to heating.

In an additional embodiment, the reaction mixture can be heated to about 70° C. for about 1 hour to obtain the heated reaction mixture.

In yet another embodiment, the heated reaction mixture can be cooled and acidified with HCl.

In an additional embodiment, the organic layers can be extracted from the crude residue by taking the crude residue in a mixture of CH$_2$Cl$_2$ and distilled water and extracting three times with CH$_2$Cl$_2$. In one embodiment in this regard, the organic layers can be dried over MgSO$_4$ and any remaining solvent can be evaporated in vacuo. In one more embodiment in this regard, the purifying can be conducted by column chromatography. In certain embodiments, the column chromatography can be conducted using an eluent of petroleum ether and dichlormethane in a 5:1 ratio, by weight.

In one more embodiment, the 2,2'-dimethyl-4,4'-diiodoazobenzene can be obtained as an orange crystalline solid.

EXAMPLES

Example 1

Synthesis of 2,2'-dimethyl-4,4'-diiodoazobenzene 4-iodo-2-methylaniline (0.07 mmol) was suspended in 20 mL HCl and 50 mL water. At 0° C. the amine group was diazotized by slowly adding a solution of NaNO$_2$ (5.8 g, 0.08 mol, 1.2 eq.) in 25 mL water. After stirring the mixture at 0° C. for 1 hr, the solution was carefully transferred via a cannula into a freshly prepared solution of CuSO$_4$·5H$_2$O (34.7 g, 0.14 mol, 2.0 eq.), NH$_4$OH (75 mL, 0.48 mmol, 6.9 eq.), NH$_2$OH (10.3 g, 0.15 mmol, 2.1 eq.) and 5 g of NaOH in 50 mL water. Then stirring was continued at 25° C., and the reaction mixture was heated up to 70° C. for 1 hr. The resulting mixture was cooled down and acidified with 25 mL HCl (37%). The crude residue was taken up in a mixture of CH$_2$Cl$_2$ and distilled water and the organic layer was extracted three times with CH$_2$Cl$_2$. The combined organic layers were dried over MgSO$_4$ and the solvent was evaporated in vacuo. Purification by column chromatography (eluent: petroleum ether/dichloromethane, 5:1) gave the desired 2,2'-dimethyl-4,4'-diiodoazobenzene as an orange crystalline solid.

$^1$H-NMR (400 MHz, CD$_2$Cl$_3$): δ 7.55 (d, 2H, $_4J_{H(3)-H(2)}$=2.0 Hz, H$_{(3)}$), 7.52 (d, 2H, $_3J_{H(1)-H(2)}$=8.6 Hz, H$_{(1)}$), 7.41 (dd, 2H, $_3J_{H(2)-H(1)}$=8.6 Hz, $_4J_{H(2)-H(3)}$=2.0 Hz, H$_{(2)}$), 2.70 (s, 6H, Me) ppm.

It is to be understood that the present method(s) of synthesis are not limited to the specific embodiments or examples described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of making a 2,2'-dimethyl-4,4'-diiodoazobenzene compound, the method comprising:
    suspending 4-iodo-2-methylaniline in a mixture of HCl and water to obtain a suspension;
    diazotizing the amine group of the 4-iodo-2-methylaniline by slowly adding a solution of NaNO$_2$ in water to the suspension to obtain a mixture;
    stirring the mixture to obtain a stirred mixture;
    transferring the stirred mixture into a solution of CuSO$_4$·5H$_2$O, NH$_4$OH, NH$_2$OH, and NaOH in water to obtain a reaction mixture;
    heating the reaction mixture to obtain a heated reaction mixture;
    cooling and acidifying the heated reaction mixture to obtain an acidified mixture;
    obtaining a crude residue;
    extracting organic layers of the crude reside; and
    purifying the organic layers to obtain the 2,2'-dimethyl-4,4'-diiodoazobenzene compound having the formula:

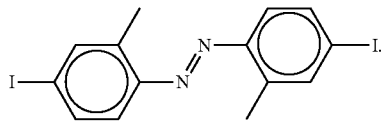

2. The method of claim 1, wherein the diazotizing step is conducted at a temperature of about 0° C.

3. The method of claim 1, wherein the mixture is stirred at about 0° C. for about 1 hour.

4. The method of claim 1, wherein the reaction mixture is stirred at 25° C. prior to heating.

5. The method of claim 1, wherein the reaction mixture is heated to about 70° C. for about 1 hour to obtain the heated reaction mixture.

6. The method of claim 1, wherein the heated reaction mixture is cooled and acidified with HCl.

7. The method of claim 1, wherein the organic layers are extracted from the crude residue by taking the crude residue in a mixture of CH$_2$Cl$_2$ and distilled water and extracting three times with CH$_2$Cl$_2$.

8. The method of claim 7, wherein the organic layers are dried over MgSO$_4$ and any remaining solvent is evaporated in vacuo.

9. The method of claim 8, wherein the purifying is conducted by column chromatography.

10. The method of claim 9, wherein the column chromatography is conducted using an eluent of petroleum ether and dichloromethane in a 5:1 ratio, by weight.

11. The method of claim 1, wherein the 2,2'-dimethyl-4,4'-diiodoazobenzene is obtained as an orange crystalline solid.

* * * * *